United States Patent
Kanayama et al.

(10) Patent No.: US 8,326,388 B2
(45) Date of Patent: Dec. 4, 2012

(54) METHOD AND APPARATUS FOR NON-INVASIVE MEASUREMENT OF LIVING BODY CHARACTERISTICS BY PHOTOACOUSTICS

(75) Inventors: Shoichi Kanayama, Koshigaya (JP); Kazuhiro Itsumi, Kawasaki (JP); Omar S. Khalil, Chicago, IL (US); Stanislaw Kantor, Buffalo Grove, IL (US)

(73) Assignee: Toshiba Medical Systems Corporation, Tochigi (JP)

( * ) Notice: Subject to any disclaimer, the term of this patent is extended or adjusted under 35 U.S.C. 154(b) by 1858 days.

(21) Appl. No.: 10/532,691

(22) PCT Filed: Oct. 28, 2003

(86) PCT No.: PCT/US03/34212
§ 371 (c)(1),
(2), (4) Date: May 5, 2006

(87) PCT Pub. No.: WO2004/042382
PCT Pub. Date: May 21, 2004

(65) Prior Publication Data
US 2007/0015978 A1    Jan. 18, 2007

(30) Foreign Application Priority Data
Oct. 31, 2002    (JP) .................................. 2002-317801

(51) Int. Cl.
*A61B 5/1455*    (2006.01)
(52) U.S. Cl. ........................................ 600/310; 600/316
(58) Field of Classification Search ........... 600/309–344
See application file for complete search history.

(56) References Cited

U.S. PATENT DOCUMENTS

| | | | |
|---|---|---|---|
| 4,028,548 A | | 6/1977 | Scott |
| 4,773,140 A | * | 9/1988 | McAusland .................. 29/25.35 |
| 5,295,487 A | * | 3/1994 | Saitoh et al. ................... 600/459 |
| 5,615,675 A | | 4/1997 | O'Donnell et al. |
| 5,941,821 A | | 8/1999 | Chou |
| 6,405,069 B1 | | 6/2002 | Oraevsky et al. |

(Continued)

FOREIGN PATENT DOCUMENTS

DE    44 00 674    7/1995

(Continued)

OTHER PUBLICATIONS

Quan, et al., Glucose determination by a pulsed photoacoustic technique: an experimental study using a gelatin-based tissue phantom, Phys. Med. Biol. 38: 1911-1922 (1993).

(Continued)

*Primary Examiner* — Eric Winakur
*Assistant Examiner* — Marjan Fardanesh
(74) *Attorney, Agent, or Firm* — Brian E. Davy; Edward J. Baba; Bozicevic, Field & Francis LLP

(57) ABSTRACT

A method and apparatus for non-invasive measurement of living body information comprises a light source configured to generate light containing a specific wavelength component, an irradiation unit configured to irradiate a subject with the light, and at least one acoustic signal detection unit including piezoelectric devices formed of a piezoelectric single crystal containing lead titanate and configured to detect an acoustic signal which is generated due to the energy of the irradiation light absorbed by a specific substance present in or on a subject.

14 Claims, 6 Drawing Sheets

U.S. PATENT DOCUMENTS

2002/0055671 A1    5/2002  Wu et al.

FOREIGN PATENT DOCUMENTS

| | | |
|---|---|---|
| EP | 0 908 241 | 4/1999 |
| JP | 9145683 | 6/1997 |
| JP | 11076239 | 3/1999 |
| JP | 2001276067 | 10/2001 |
| KR | 1999-0045525 | 6/1999 |

OTHER PUBLICATIONS

Christison et al., Laser photoacoustic determination of physiological glucose concentrations in human whole blood, Medical & Biological Engineering & Computing, 31: 284-290 (1993).

* cited by examiner

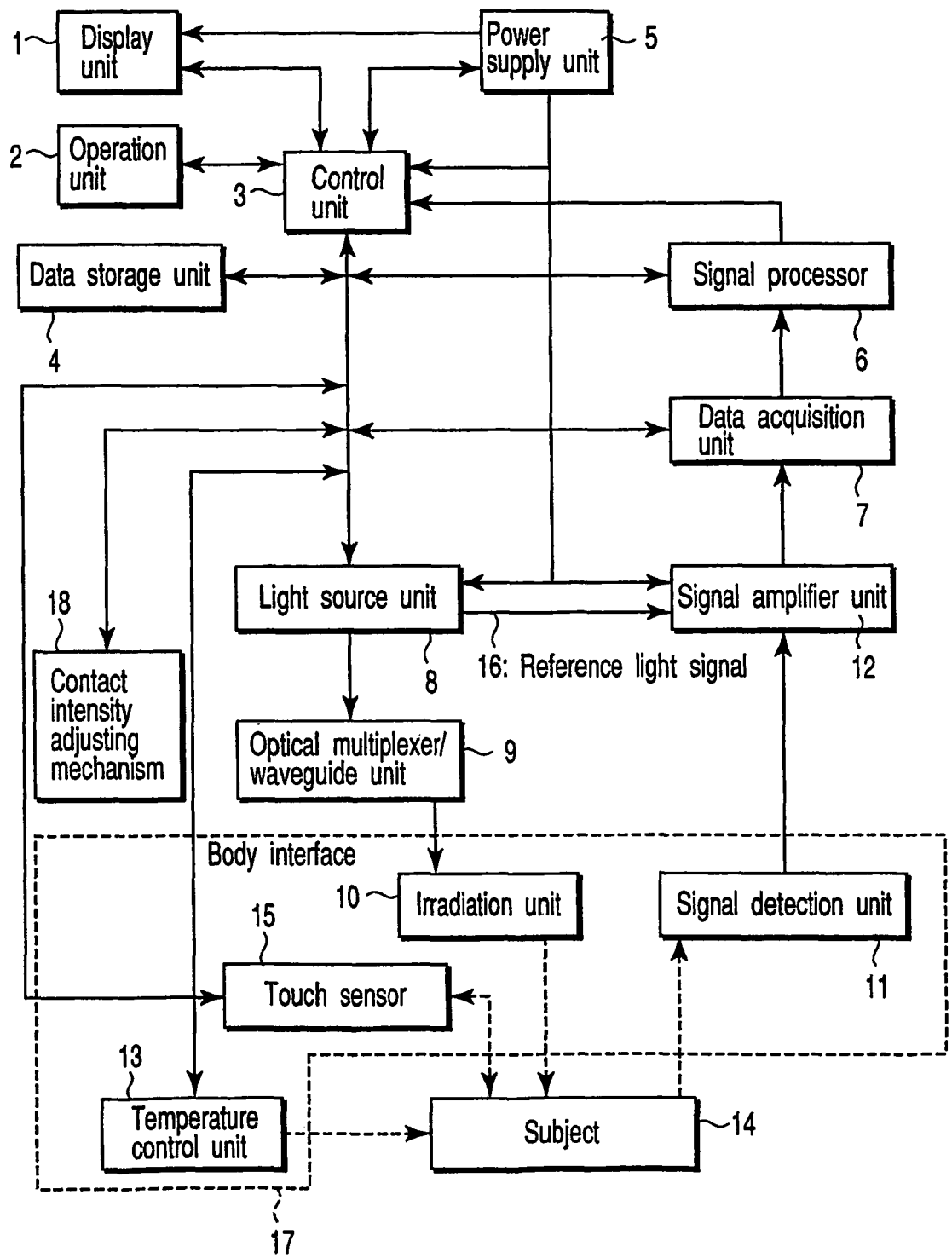
F I G. 1

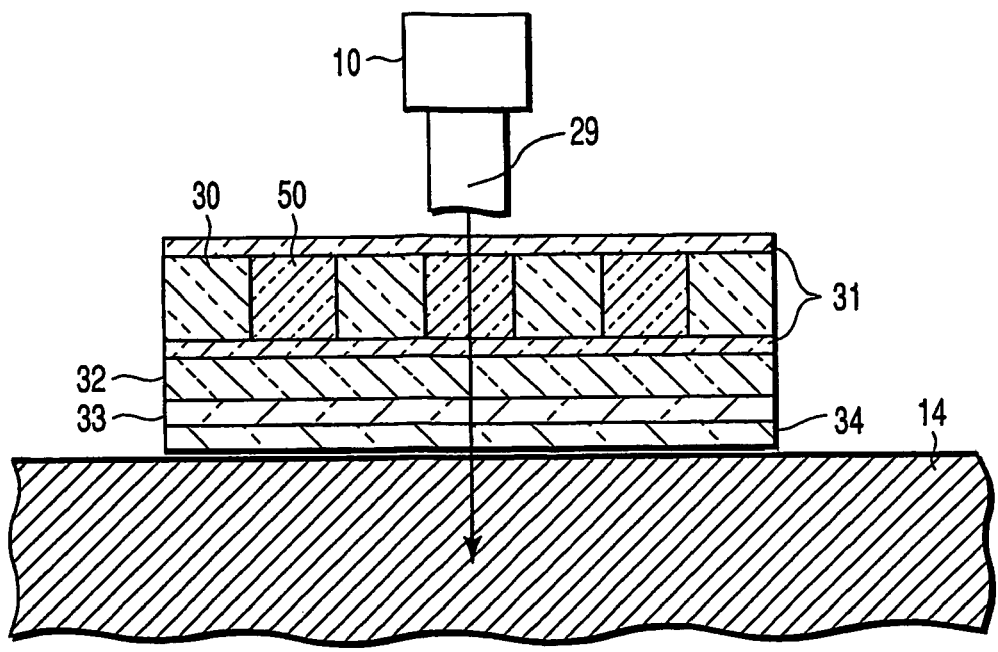
F I G. 9
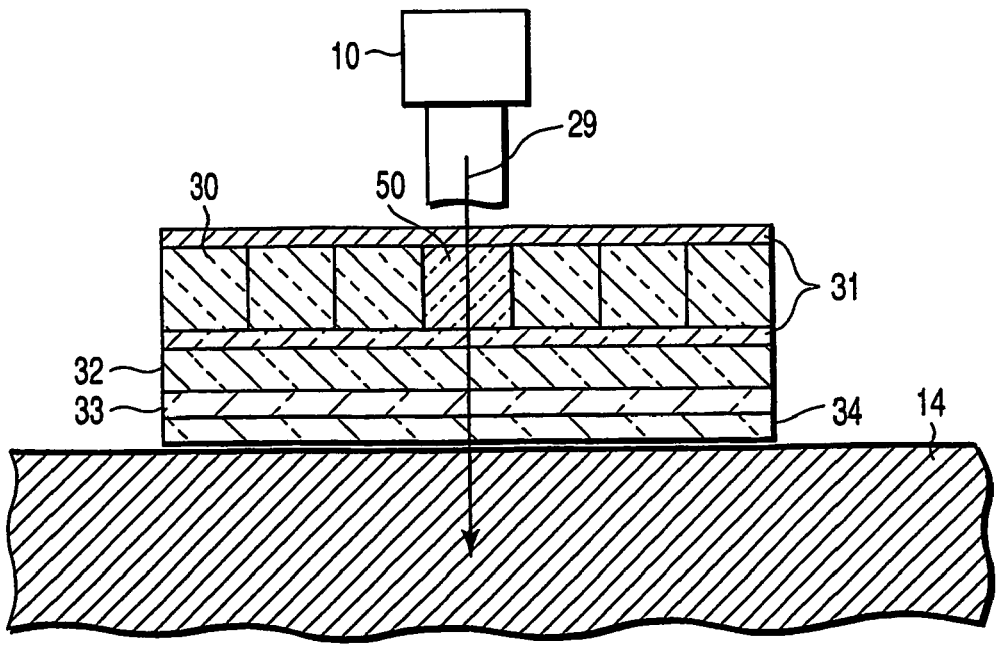
F I G. 10

METHOD AND APPARATUS FOR NON-INVASIVE MEASUREMENT OF LIVING BODY CHARACTERISTICS BY PHOTOACOUSTICS

CROSS-REFERENCE TO RELATED APPLICATIONS

This application is based upon and claims the benefit of priority from the prior Japanese Patent Application No. 2002-317801, filed Oct. 31, 2002, the entire contents of which are incorporated herein by reference.

BACKGROUND OF THE INVENTION

1. Field of the Invention

This invention relates to a method and apparatus for non-invasively measuring at least one parameter of a sample, such as the presence and/or concentration of one or more analytes or physical and/or chemical constants characterizing the tissue in a human body part by using photoacoustic spectroscopy.

2. Description of the Related Art

Analysis of samples and measurement of the concentration of components contained therein is a common and important process in chemistry and biology. In particular, the analysis of the biological fluids such as blood, interstitial fluid, urine or saliva to determine the concentrations of various components and to determine the diseases state is important both in diagnosis and in treatment of a variety of diseases including diabetes and cardiac diseases. The measurement of physical and/or chemical constants characterizing the tissue is also effective in diagnosis of various diseases, such as tumors. A representative apparatus for measuring the concentration of an analyte in the blood is the blood glucose meter used by diabetics. Present blood glucose meters for self-testing use a small blood sample taken from the subject by the subject, e.g. by piercing a finger or arm with a needle or lancet, to measure the subject's blood glucose level. An enzyme electrode, for example, is used for measuring the amount of glucose. An enzyme called glucose oxidase (GOD) is fixed on the macromolecule film of the electrode. When blood contacts the film, glucose in the blood reacts with oxygen in the presence of GOD. The glucose concentration can be quantified by measuring the change of oxygen consumed. Currently available blood glucose meters are portable, and are used in management of a diabetic's blood glucose level.

However, the above mentioned method is painful and damages the skin of the subject because it is necessary to prick a part of the body with a needle or a lancet. Therefore, although 5 times or more frequent monitoring in a day is desirable to manage a diabetic's blood glucose level strictly, it is currently restricted to 2 or 3 times per day.

The minimally invasive skin microporation approaches utilizing laser or ultrasound for extracting the blood or the interstitial fluid are disclosed in U.S. Pat. No. 6,074,383 and No. 5,458,140. On the other hand, non-invasive monitoring methods and apparatus using visible light and/or near-infrared light which neither require pricking a part of the body with the a needle or a lancet nor to extract the sample such as blood or interstitial fluid are disclosed in Japanese patents kokai No. 60-236631 and kokai No. 02-191434. The non-invasive measurement, which can determine an analyte or a disease state in a human subject without performing any invasive procedures such as removing a sample of blood or a biopsy specimen, has several advantages. The advantages include ease of use, reduced pain and discomfort, and decreased exposure to potential biohazards.

Visible light here means electromagnetic waves in the range of about 380 nm to about 770 nm; near-infrared light means electromagnetic waves in the range of about 770 nm to about 1500 nm; middle-infrared light means electromagnetic waves in the range of about 1500 nm to about 3000 nm; far-infrared light means electromagnetic waves in the range of about 3000 nm to about 25000 nm.

The above mentioned Japanese patent applications disclose the methods for glucose concentration measurement of the subject such that the near-infrared light of plural wavelengths is irradiated on the skin surface of the subject, and the light which is diffused and/or scattered in the subject is detected, and the detected signals are divided into a reference signal and objective signal, and the glucose concentration is calculated from these signals. It is also disclosed that a tungsten halogen lamp, semiconductor laser (LD), or light emitting diode (LED) can be used as the light source for near-infrared light, and a photodiode (PD) can be used as the detector of the diffused and or scattered infrared light.

Non-invasive spectroscopic monitoring of biological substances using the visible and/or near-infrared light has advantages over using middle-infrared or the far-infrared light. These are high tissue penetration and high analyses capability for the aqueous solution because it has low absorption by water—the main constituent of the human body.

On the other hand, the non-invasive spectroscopic monitoring using the visible and/or near-infrared lights also has disadvantages. The signal which is attributable to molecular vibration is as low as about one-hundredth ($\frac{1}{100}$), and is hard to specify an attribution of the signal as compared with that using the middle- or far-infrared light.

Other methods of non-invasive glucose measurement are also disclosed in U.S. Pat. No. 5,348,002, Japanese patent kokai No. 10-189, and Japanese patent kokai No. 11-235331. These patents disclose methods and glucose concentration measurement apparatuses using near-infrared light irradiated onto the skin of the subject, and a photoacoustic signal generated with result that glucose molecules in the subject absorb energy of the irradiation is detected by a detection means. In photoacoustic spectroscopy disclosed in the patents, a microphone device or a piezoelectric vibrator such as lead zirconate titanate (PZT) ceramics is generally used as the detection means.

However, it is a difficult to get photoacoustic signals with good signal to noise ratio that are adequate for measuring glucose concentration, even after using repetitive measurements and signal averaging, because the generated photoacoustic signals are so weak.

The above-mentioned methods and apparatus for non-invasive monitoring are applicable to other substances and analytes besides glucose, for example, cholesterol, natural fats, and hemoglobin.

BRIEF SUMMARY OF THE INVENTION

It is accordingly the object of the present invention to provide a method and an apparatus for non-invasive measurement of a living body which can highly accurately measure a very faint acoustic signal which is generated due to the energy of irradiation light absorbed by a specific substance in or on the subject.

In a first aspect of the present invention there is provided an apparatus for non-invasive measurement of a living body, comprising; a light source configured to generate light containing a specific wavelength component, an irradiation unit configured to irradiate a subject with the light, and at least one acoustic signal detection unit including piezoelectric devices formed of a piezoelectric single crystal containing lead titanate and configured to detect an acoustic signal which is generated due to the energy of the irradiation light absorbed by a specific substance present in or on a subject.

In a second aspect of the present invention there is provided an apparatus for non-invasive measurement of a living body, comprising, a light source configured to generate light containing a specific wavelength component, an irradiation unit configured to emit the light, and an acoustic signal detection unit having an optical transparency to the specific wavelength component of the light, arranged between a subject and the irradiation unit and configured to detect an acoustic signal which is generated due to the energy of the light absorbed by a specific substance present in or on the subject, wherein the light emitted from the irradiation unit is applied as irradiation light to the subject through the acoustic signal detection unit.

In a third aspect of the present invention there is provided an apparatus for non-invasive measurement of living body information, comprising a light source configured to generate light containing a specific wavelength component, an irradiation unit configured to irradiate the light as irradiation light to a subject, and an acoustic signal detection unit having a piezoelectric device optically transparent to the specific wavelength component of the light and configured to detect an acoustic signal which is generated due to the energy of the irradiation light absorbed by a specific substance present in or on the subject.

In a fourth aspect of the present invention there is provided a method for non-invasive measurement of living body information comprising, outputting light containing a specific wavelength component generated by a light source from an irradiation unit, irradiating a subject with light from the irradiation unit through at least one acoustic signal detection unit including piezoelectric devices formed of a piezoelectric single crystal containing lead titanate, and detecting an acoustic signal which is generated due to the energy of the light absorbed by a specific substance present in or on the subject by the acoustic signal detection unit.

In a fifth aspect of the present invention there is provided a method for non-invasive measurement of a living body comprising, outputting light containing a specific wavelength component generated by a light source from an irradiation unit, irradiating a subject with light output from the irradiation unit through at least one acoustic signal detection unit having an optical transparency to light, and detecting an acoustic signal which is generated by the energy of the light absorbed by a specific substance present in or on the subject by the acoustic signal detection unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a schematic diagram showing a structure of an apparatus for non-invasive measurement of living body information, associated with the first embodiment of the invention.

FIG. 9 is a cross-sectional view showing a light irradiation/photoacoustic signal detection unit in a variant of the fourth embodiment.

FIG. 10 is a cross-sectional view showing a light irradiation/photoacoustic signal detection unit in a variant of the fourth embodiment.

DETAILED DESCRIPTION OF THE INVENTION

Figure 2:
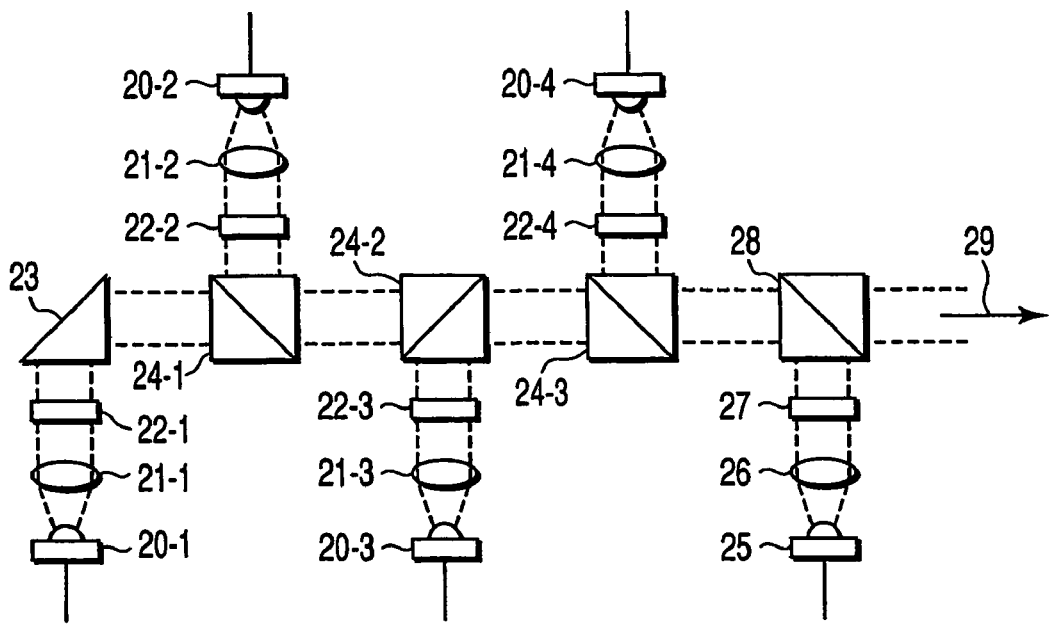
FIG. 2 is a schematic diagram showing a portion of the apparatus, particularly the light source unit and the optical wavelength multiplexing unit, associated with the first embodiment of the invention.

FIG. 1 is a schematic diagram of an apparatus for non-invasive measurement of living body information, associated with the first embodiment of the present invention. In FIG. 1, a light source unit 8 radiates one or more monochromatic light beams or light beams with a desired center wavelength and bandwidth. When there are two or more light beams radiated from the light source unit 8, they are multiplexed by an optical multiplexer/waveguide unit 9. Then, the light beams are guided to an irradiation unit 10 through the optical waveguide constituted as a part of the optical multiplexer/waveguide unit 9, such as an optical fiber, an optical thin film waveguide or free space, and the light is irradiated onto a measurement site of a subject 14 by the irradiation unit 10. Moreover, the light source unit 8 generates a reference light signal 16 which may be electric signal(s) and in proportion to the intensity of each monochromatic light or light with a desired center wavelength and bandwidth.

The acoustic signal that is generated in the subject 14 by irradiating the light is detected and converted into an electric signal by a photoacoustic signal detection unit 11. The electric signal and the reference light signal 16 are amplified to adequate amplitudes in a signal amplifier unit 12 and are then transmitted to a data acquisition unit 7. The photoacoustic signal detection unit 11 has a piezoelectric element consisting of a solid solution system of a piezoelectric single crystal including at least lead titanate as a main component.

The piezoelectric single crystal is fabricated by the following method, for example. PbO, ZnO, $Nb_2O_5$, and $TiO_2$ are used as the starting materials. The weights of the starting materials are measured such that lead zinc niobate (PZN) and lead titanate (PT) satisfy a molar ratio of 91:9. Thereafter, the materials are heated to 1260° C. for 5 hours, then gradually cooled down to 800° C. at a cooling rate of 0.8° C./hr, and finally allowed to be cooled down to the room temperature.

Thereafter, the [001] axis of the resultant single-crystal is detected by making use of a Laue X-ray camera, and the single-crystal is sliced perpendicular to the [001] axis with a dicing saw, is lapped to a thickness of 0.2-5 mm, and Ti/Au electrodes are formed by sputtering on its opposite surface. These single crystal wafers are subjected to a polarization process that heats the wafers to 200° C. in silicone oil, and then cools them down to 40° C. while applying an electric field of 1 kV/mm. The resultant vibrators are diced with a dicing saw into a size of 5-10 mm, thus piezoelectric single crystals (a solid solution system of a piezoelectric single crystal) obtained by the above-mentioned process are used as the signal detection unit. The piezoelectric single crystal can now be called a PZNT single crystal. The piezoelectric constant g33 of a PZNT single crystal is about $43 \times 10^{-3}$ Vm/N, and this is about 1.7 times larger than that of general piezoelectric ceramics $g_{33}$ ($25 \times 10^{-3}$ Vm/N).

The irradiation unit 10, the photoacoustic signal detection unit 11, temperature control unit 13, and touch sensor 15 constitute a body interface 17 which contacts the subject 14. The temperature control unit 13 is arranged around the measurement site of the subject 14, and controls the temperature of the site. A thermoelectric cooler such as a Peltier device that can control temperature by changing the applied current or voltage can be used as the temperature control unit 13. For example, the temperature of the measurement site is controlled to a constant temperature between 20° C. and 40° C. by the temperature control unit 13. Because photoacoustic signals are affected by the temperature of the measurement site, temperature control of the measurement site improves measurement accuracy.

Photoacoustic signal measurement is also affected by the degree of contact between the measurement site in the subject 14 and the body interface 17. The touch sensor 15 detects the degree of contact of the measurement site and the body interface 17, and the signal of the touch sensor 15 is used to control the measurement protocol. For example, measurement is performed when the measurement site and the body interface 17 fully touch. When there is no subject or no object in contact with the body interface 17, it is also possible to avoid risks, such as damage to the ophthalmus by the irradiation light, by controlling not to emit the light to the exterior of the apparatus by the control unit 3. For example, the devices that measure pressure or electrical resistance can be used as the touch sensor 15. Furthermore, a device for adjusting the degree of contact of the measurement site and the body interface 17 can be attached in a part of the body interface 17, and the device can be controlled by the signal of the touch sensor 15. A mechanical actuator, or piezoelectric actuator can be used as the device.

Further, a degree-of-contact adjusting mechanism 18 can be provided at the interface 17 to adjust the degree of contact between the measurement site of the subject 14 and the interface 17. The degree of contact can be adjusted by a signal from the touch sensor 15. As the adjusting mechanism 18 use can be made of a mechanical actuator for actuating the interface 17 or a portion thereof, and a piezoelectric actuator utilizing the displacement of the piezoelectric device. If the degree of contact detected by the touch sensor 15 is unduly high, this could mean that an unduly strong stimulus or damage is inflicted on the measurement site of the subject 14. In order to avoid such a risk, any safety measure can be secured to stop the measuring operation itself, such as stopping the irradiation light. The level of safety can be further enhanced by controlling the adjusting mechanism 18 by the control unit 3 such that, in unison with the stopping of the measurement operation, the interface 17 is moved away from the measurement site. If the degree of contact detected by the touch sensor 15 is not within a normal range, control is performed by adjusting the degree of contact, or stopping the irradiation of light, etc., so as to maintain safety.

The electric signals that are transmitted to the data acquisition unit 7 are digitized and acquired in the data acquisition unit 7. The digital signals are used for signal processing in a signal processing unit 6 to obtain the desired body information. Then, the results of the signal processing which include the desired body information are stored in a data storage unit 4 and displayed on a display unit 1 if needed. The method of indication on the display unit 1 is a visual communication method such as indication on screen, or an auditory communication method such as a voice tone, or a tactile communication method such as a vibration, or a combination of these methods. The operation unit 2 can be used by the subject or another operator. The user interface of the operation unit 2 can be a keyboard, mouse, button, touch-key-panel, voice recognition device, or a combination of these devices.

The control unit 3 controls the display unit 1, data storage unit 4, power supply unit 5, signal processor 6, data acquisition unit 7, light source unit 8, signal amplifier unit 12, and the temperature control unit 13 according to the control signal from the operation unit 2, the output signal from the touch sensor 15, and so on.

In the light source unit 8, it is preferable to use one or plural light emitting devices such as a laser diode (LD) or light-emitting diode (LED) emitting a specific wavelength component within a range of 600 to 5000 nm. As an example of the present invention, light of a wavelength range from 400 nm to 2500 nm is irradiated onto the measurement site of the subject 14 to measure the glucose concentration in the subject 14. As materials for the LD or LED, InGaAlP for the wavelength range from 550 nm to 650 nm, GaAlAs for the wavelength range from 650 nm to 900 nm, and InGaAs or InGaAsP for the wavelength range from 900 nm to 2300 nm can be used. A light emitting device made of InGaN can be also used for light of 550 nm wavelength or less.

FIG. 2 is a schematic diagram showing a portion of the apparatus, particularly the light source unit 8 and the optical wavelength multiplexing unit 9, associated with the first embodiment of the invention. The light sources 20-1, 20-2, 20-3 and 20-4 emit light of different wavelengths. The intensities and the modulation frequencies of the emitted light beams are controlled by a signal from the control unit 3, which controls the drive currents supplied to each light source. Each light beam is collimated through collimate lens 21-1, 21-2, 21-3 and 21-4, and filtered through optical filters 22-1, 22-2, 22-3 and 22-4 to eliminate undesired characteristics and/or adjust the optical intensity. Then, the light beams of different wavelengths are multiplexed on an optical axis by a right-angle prism 23 and dichroic prisms 24-1, 24-2 and 24-3.

The synthesized light is divided into an output light beam 29 and a reference light beam by a beam splitter 28. The reference light enters a photodetector 25 through an optical filter 27 and a focus lens 26. The photodetector 25 detects the reference light and outputs an electrical reference signal. In this example, four light sources are shown. However, the present invention is not limited to this, it is possible to use any number of light sources. A commercially available multiplexing device for optical communication may also use as the optical wavelength multiplexing unit 9.

The output light 29 is transmitted to the irradiation unit 10 by free space propagation or through an optical waveguide such as an optical fiber or an optical thin film waveguide. The beam spot that irradiates the subject 14 from the irradiation unit 10, for example, has a circular and uniform light intensity distribution with a diameter of about 0.4 mm. The power of the light irradiated is below the maximum permissible exposure (MPE) described in Japanese Industrial Standards JIS C 6802 "Radiation safety of laser products" in order not to inflict damage on living body tissue.

Figure 3:
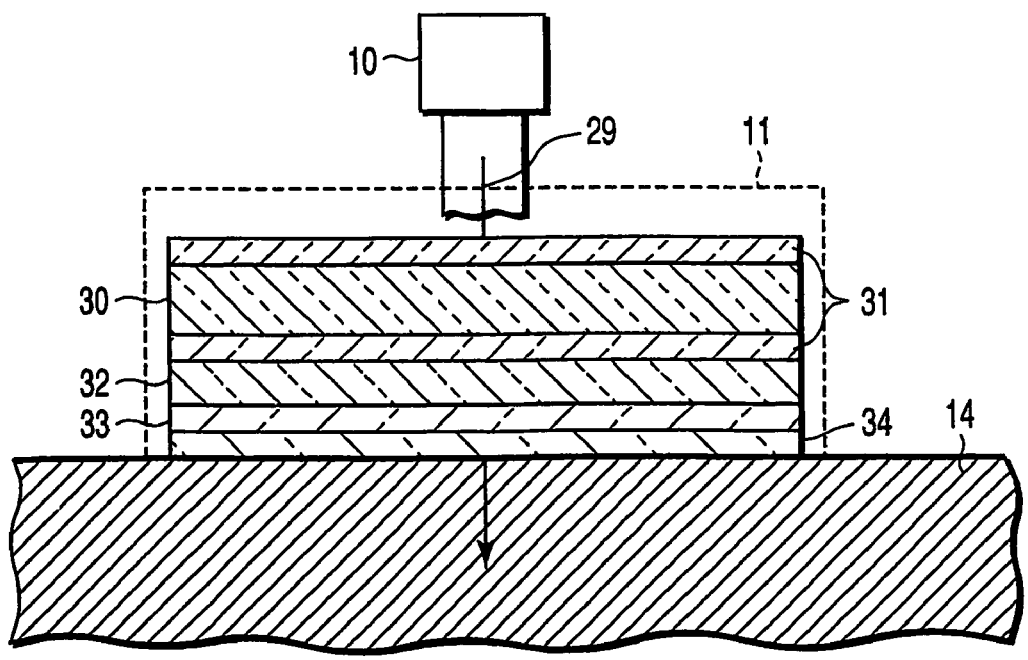
FIG. 3 is a schematic diagram showing a structure of an apparatus for non-invasive measurement of living body information, associated with the second embodiment of the invention.

FIG. 3 is a schematic diagram showing the structure of the apparatus for non-invasive measurement of a living body according to a second embodiment of the present invention. The above-mentioned PZNT single crystal 30 is used for the photoacoustic signal detection unit 11. The PZNT single crystal 30 has high permeability in the wavelength range of visible light to near-infrared light, and the transmittance is typically about 70% in the wavelength range of 400-6000 nm. A transparent conductive material, which is used for the liquid crystal display and the plasma display, such as ITO (Indium Tin Oxide, $In_2O_3(Sn)$), is used as an electrode 31. The electrodes 31 are formed on both principal plane surfaces of the PZNT single crystal 30 by sputtering.

Furthermore, in order to make matching of the acoustic impedance with the subject 14, the acoustic matching layers 32 and 33 are formed on one of the electrodes 31. Epoxy resin, which is optically transparent can be used for the acoustic matching layers. For example, a resin that has an acoustic impedance of about $7 \times 10^6$ kg/m$^2$s can be used for the acoustic matching layer 32, and a resin that has an acoustic impedance of about $3 \times 10^6$ kg/m$^2$s can be used for the acoustic matching layer 33.

The reliability of the photoacoustic signal detection unit 11 can be improved by forming a thin film 34 for protection on the contact surface of the subject 14. A silicon resin, which has optically transparency, can be used for this thin film 34. The output light 29 can be irradiated onto the subject 14 through the photoacoustic signal detection unit 11 because the light is enabled to pass through the photoacoustic signal detection unit 11 by the constitution of FIG. 3.

It is desirable that the optical refractive index of the PZNT single crystal 30, the acoustic matching layers 32 and 33, and the thin film 34 are equivalent or similar. An objective lens or an optical device for controlling the irradiation site of the subject 14 can be arranged between the acoustic matching layer 33 and the thin film 34 if necessary.

The irradiation unit 10 and the photoacoustic signal detection unit 11 can be integrated and miniaturized easily because the light passes through the signal detection unit 10 and is irradiated onto the subject 14. Therefore, two or more irradiation and detection units can also be arranged in a matrix, for simultaneous multipoint monitoring and can obtain a distribution for the body information such as glucose concentration. Moreover, since the position for irradiation and acoustic signal detection can be made identical, the detection efficiency of the acoustic signal can be improved.

Figure 4:
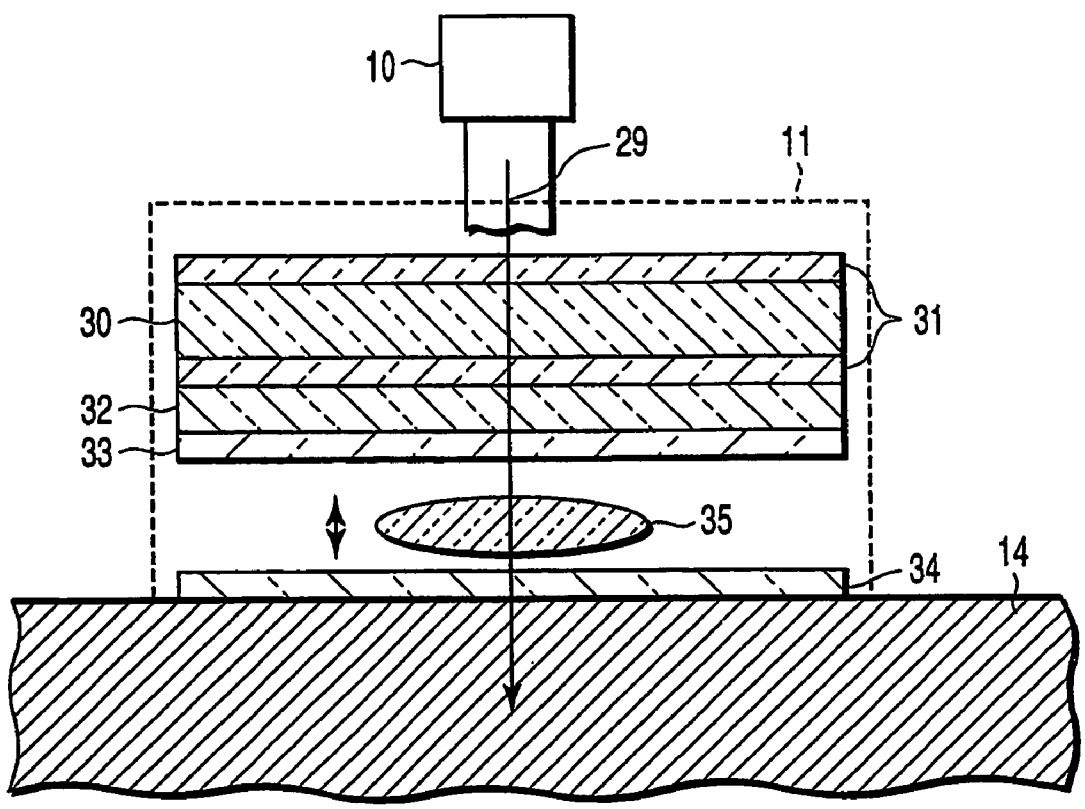
FIG. 4 is a cross-sectional view of a acoustic signal detection unit having an objective lens in a variant of the second embodiment.

Note that, as shown in FIG. 4, a forward/backward movable objective lens 35, or an optical waveguide, for controlling the irradiation site of the subject 14 may be arranged between the acoustic matching layer 33 and the protective thin film 34. By allowing the beam which is irradiated from the irradiation unit 10 to be directed past the photoacoustic signal detection unit 11 onto the subject, it is possible to construct the irradiation unit 10 and photoacoustic signal detection unit 11 as an integral and compact unit.

Figure 5:
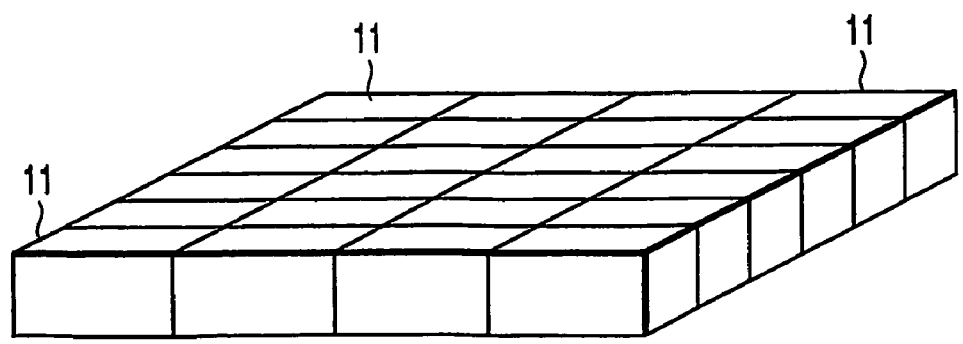
FIG. 5 is a perspective view of an array of acoustic signal detection units in a variant of the second embodiment.

As shown in FIG. 5, therefore, plural signal detection units 11, together with plural irradiation units 10, can be arranged in a matrix, in a high integration density structure. With this structure, the control unit 3 enables a spatial distribution of the living body characteristics, for example, a glucose or hemoglobin concentration distribution in the subject, to be created in a two- or three-dimensional way on the basis of plural living body characteristics detected at different detection positions by means of plural signal detection units 11. Further, since the distance between the beam irradiation position and the signal detection position can be maintained constant, it is possible, by optimizing this distance, to maximize the detection efficiency of the acoustic signal and hence to enhance the measuring accuracy.

In order to obtain a spatial distribution of living body characteristics in the two- or three-dimensional way, a moving mechanism can be provided for moving the irradiation unit 10 instead of providing plural irradiation units 10. In this case, the irradiation unit 10 is moved by the moving mechanism over an array of signal detection units 11 as shown in FIG. 5 to allow the irradiation position of the light to be changed and the living body information to be detected at a different detection position (a two- or three-dimensional position). The arrayed signal detection unit side may be so configured as to allow corresponding signals to be detected by all the signal detection units 11 or, in accordance with change in the irradiation position, allow a corresponding signal to be detected at its switched photoacoustic signal detection unit 11. Further, the moving mechanism could be made to move the irradiation unit 10 and photoacoustic signal detection unit 11. In this case, the living body characteristics can be detected at different positions (two- or three-dimensional positions) by moving the irradiation unit 10, by means of the moving mechanism, to a corresponding light irradiation position and also moving the photoacoustic signal detection unit 11 to that position.

According to the present embodiment, the signal detection unit is formed of a transparent piezoelectric device using a solid solution system of a piezoelectric single crystal containing lead titanate and it is possible to locate the signal detection unit between the light irradiation unit and the subject. By doing so it is possible to vertically direct the irradiation light onto the subject and to vertically receive an acoustic signal from the subject through the piezoelectric device. It is, therefore, possible to enhance the detection efficiency of the acoustic signal and detect it with high sensitivity and hence to improve the measurement accuracy. Further, the irradiation unit and signal detection unit can be constructed as an integral structure, thus enabling a resultant apparatus to be realized as a compact unit.

Figure 6:
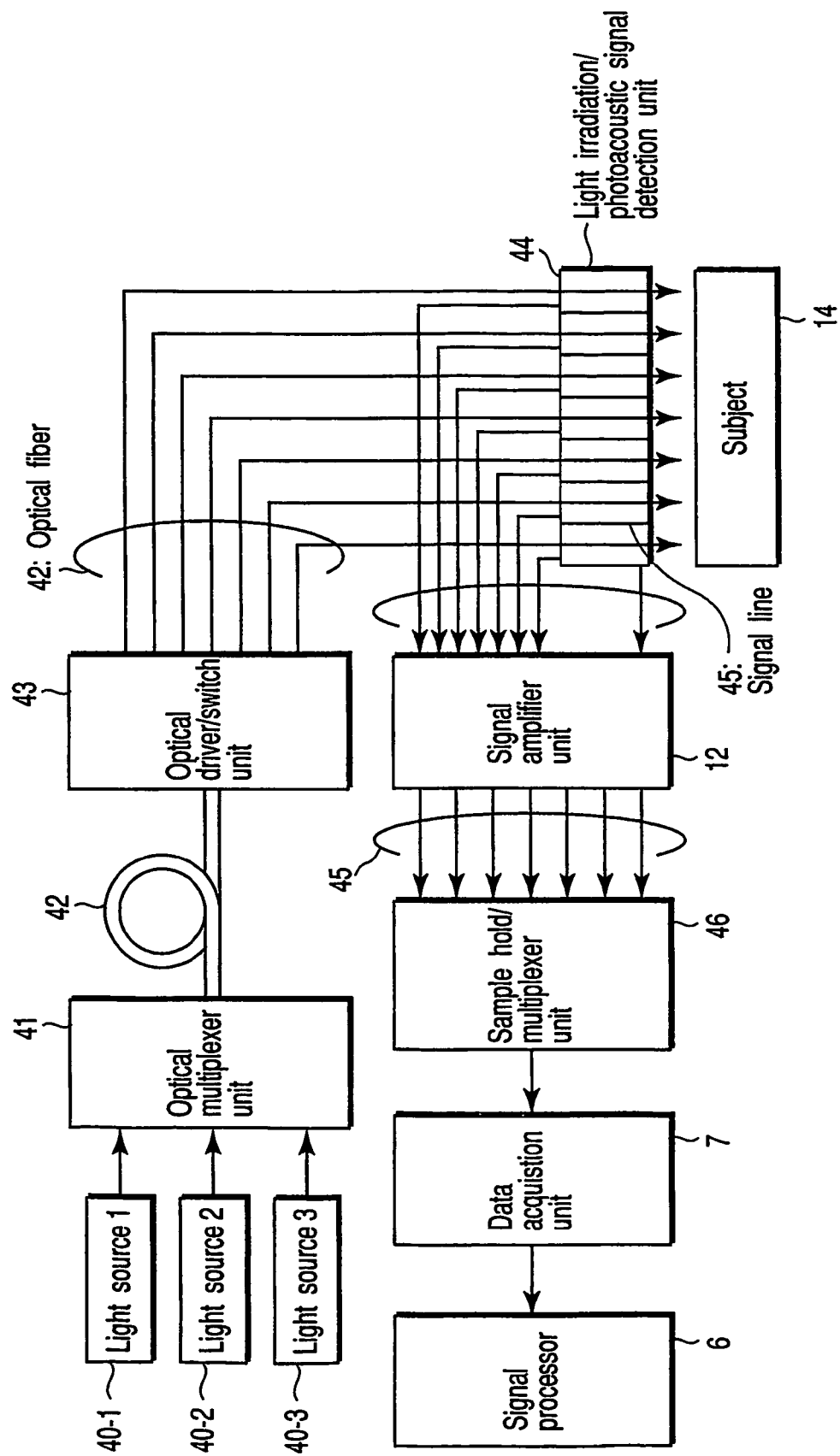
FIG. 6 is a schematic diagram showing a structure of an apparatus for non-invasive measurement of living body information, associated with the third embodiment of the invention.

FIG. 6 is a schematic diagram showing the structure of the apparatus for non-invasive measurement of living body characteristics, associated with the third embodiment of the invention. The light beams of two or more wavelengths emitted from the light sources 40-1, 40-2 and 40-3 are multiplexed on an optical axis by an optical multiplexer unit 41. The synthesized light is transmitted to an optical divider/switch unit 43 through an optical fiber 42 and is divided, branched, or demultiplexed by the optical divider/switch unit 43. The optical divider/switch unit 43 also controls whether the irradiation light beams are irradiated onto the subject 14 through the optical fiber 42 and light irradiation/photoacoustic signal detection unit 44.

The light irradiation/photoacoustic signal detection unit 44 has two or more illumination channels and/or signal detection channels in order to enable simultaneous measurement at two or more sites. The acoustic signals, depicted in FIG. 6 as signal lines (e.g., signal line 45), emitted from the subject 14 by irradiating the light, are detected in the light irradiation/ photoacoustic signal detection unit 44, are then amplified by the signal amplification unit 12, and transmitted to the data acquisition unit 7 through a sample hold/multiplexer unit 46. The acoustic signals from all signal detection channels can also be collected simultaneously. The data, which is acquired in the data acquisition unit 7, is processed in the signal processing unit 6 to obtain the desired body characteristics of the subject 14.

Figure 7:
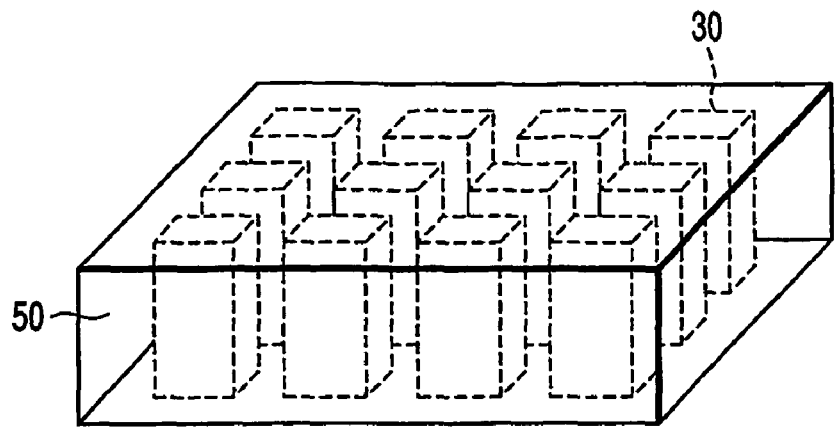
FIG. 7 is a schematic diagram showing a structure of the apparatus, particularly a piezoelectric material-polymer composite sensor for detecting the acoustic signal, associated with the fourth embodiment of the invention.
Figure 8:
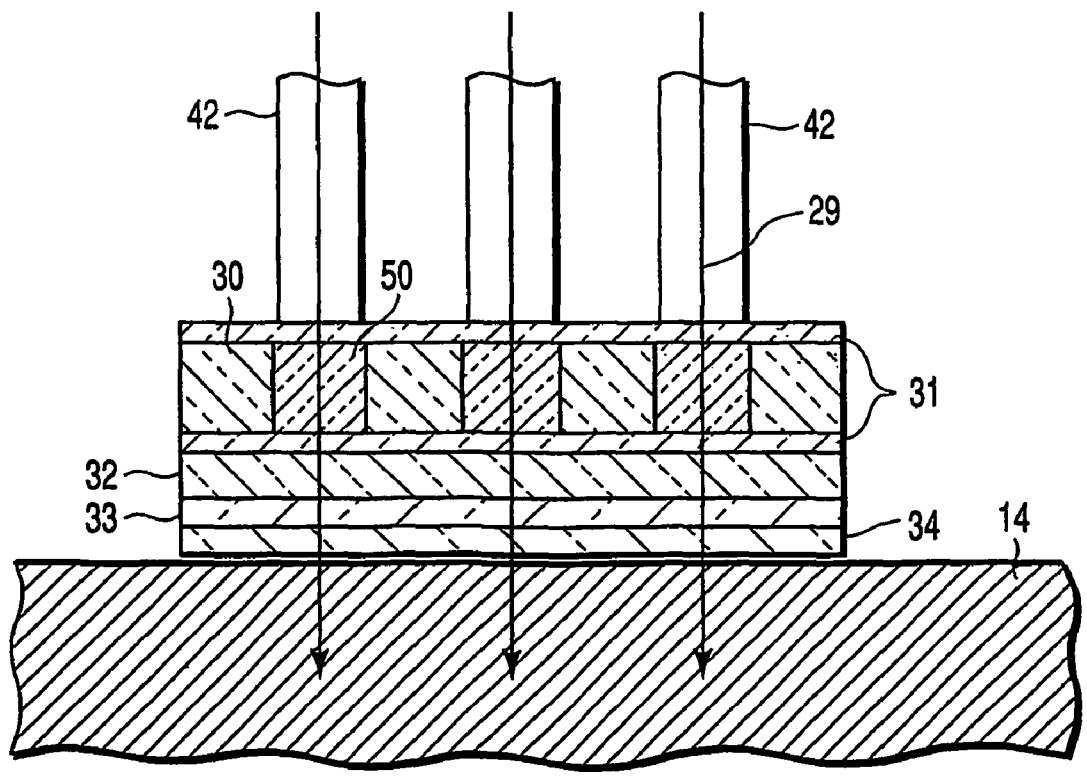
FIG. 8 is a cross-sectional view showing a light irradiation/photoacoustic signal detection unit of an apparatus for non-invasive measurement of living body information, associated with the fourth embodiment of the invention.

FIG. 8 is a schematic diagram showing the structure of the apparatus, particularly the piezoelectric material-polymer composite sensor for detecting the acoustic signal, according to the invention. FIG. 7 is a schematic diagram showing the structure of the apparatus for non-invasive measurement of living body characteristics, according to the fourth embodiment of the invention. The method of fabricating the piezoelectric material-polymer composite sensor shown in FIG. 7 will be described next.

First, a PZNT single crystal wafer is prepared as mentioned previously. The wafer is lapped into a thickness of about 0.5-5 mm, and dicing is performed using a dicing saw with a blade of 0.1-0.6 mm thickness. The half cut method of dicing is used, that is, the rest of cutting is about 0.05 mm and the dicing pitch is 0.5-1 mm. An epoxy resin is injected into the kerfs, then cured. The acoustic impedance of epoxy resin is $3 \times 10^6$ kg/m²s, and it is also optically transparent. Next, similar kerfs are formed perpendicularly to the previous kerfs and epoxy resin is injected into the those kerfs, and cured. Then, the final cutting is eliminated by lapping and ITO electrodes are formed on both sides by sputtering. The piezoelectric material-polymer composite sensor is thus completed.

The piezoelectric material-polymer composite sensor shown in FIG. 7 is called a 1-3 type structure, and has a structure where the piezoelectric rods 30 are embedded in a matrix in a substrate made of the resin 50. The electromagnetic coupling factor of this piezoelectric material-polymer composite sensor can reach 85% or more.

As shown in FIG. 8, the acoustic matching layers 32, 33 and the thin film 34 are formed on both sides of the piezoelectric material-polymer composite sensor. The optically transparent resins are used for the acoustic matching layers 32, 33 and the thin film 34 similar to the second embodiment of invention. The output light 29 can be irradiated onto the subject 14 because it can pass through the light irradiation/photoacoustic signal detection unit 44.

A PZT ceramics, which is optically opaque, can also be used instead of the piezoelectric crystal rod 30. In this case, the output light 29 passes through the optically transparent substrate of the resin 50 of the piezoelectric material-polymer composite sensor and is irradiated onto the subject 14.

In the above-mentioned example, the method for fabricating a 1-3 type piezoelectric material-polymer composite sensor is described, but the method can be changed. For example, full cutting of the single crystal may be carried out first, or it may be cut in a matrix firstly, and then filled with resin. Moreover, it may be unnecessary to eliminate an uncut portion part completely. They similar to that of a 2-2 type structure. Furthermore, a different resin can be used in each fabrication process if the epoxy resin is filled in two stages. A process for repolarization may be performed after fabricating the piezoelectric material-polymer composite sensor.

In the above, examples of the piezoelectric single crystal using a solid solution system of zinc niobate and lead titanates are described. These materials are also replaceable. For example, Mg, Ni, Sc, In and Yb can be used instead of Zn, or Nb can be replaced by Ta. Moreover, the piezoelectric single crystal can be grown using a flux method, Bridgman method, Kyropoulous method (a melt pulling method), zone melting method, hydrothermal growth method, and so on. In the above, the electrodes are formed by sputtering. However, another method such as a baking, or vapor deposition can be used. When the optical refractive index and transmittance of the piezoelectric single crystal 30 are made equal or similar to that of the resin part 50, the output light 29 can pass through any part of the piezoelectric material-polymer composite sensor.

Instead of using optical fiber 42, the irradiation unit 10 may be located above the composite structure of the piezoelectric device 30 and resin part 50 as shown in FIG. 9.

As shown in FIG. 10, a plurality of piezoelectric devices 30 may be arranged as a close-packed array with a transparent resin part 50 formed at a light irradiation path only.

The non-invasive measurement of glucose concentration in the subject 14 will be described below as a more detailed example of measuring the living body information. In order to obtain an acoustic signal derived from a desired molecule in the subject 14, light beams (an electromagnetic wave) of plural wavelengths (400 to 2,500 nm) in an absorption spectrum band of a glucose molecule, water molecule, etc., are individually applied in a pulse-like form on a skin surface of the subject 14. At this time, the respective irradiation light beams are applied to the subject 14 through the irradiation unit 10 constituting part of the interface 17. At this time, the desired molecule which absorbs the energy of the respective light beam applied to the subject 14 generates an acoustic signal. Here it is supposed that one of those acoustic signals derived from at least the desired molecule is an acoustic signal derived from the glucose molecule. The acoustic signal is detected by the acoustic signal detection unit 11 at a skin surface portion of the subject (for example, at a portion near the skin of a finer joint position through which the blood vessel runs. Each signal is processed at the signal processor 6 and an acoustic signal derived from the glucose molecule is extracted and the glucose concentration in the subject 14 is calculated from that signal intensity.

In addition to the glucose concentration, it is also possible to measure the distribution of the blood in the subject by applying an electromagnetic wave (light of one or more wavelengths selected from a wavelength range of, desirably 500 to 1,600 nm) having an absorption band characteristic of the hemoglobin in the blood for example and to identify an affected tissue in the living body, such as a cancerous tissue containing a greater amount of blood. Or it is possible to measure an amount of water in the tissue of the subject by applying an electromagnetic wave corresponding to the absorber of the water molecule.

The invention can be modified in ways not described above, to arrive at the same effect. For example, the optical signal which is returned by dispersion and reflection from the surface and/or from inside the subject 14 can be measured almost simultaneously by arranging photo detector(s), such as photodiodes, near the photoacoustic signal detection unit 11 or the light irradiation/photoacoustic signal detection unit 44, and the acoustic signal and the optical signal can be used for quantitative analysis or qualitative analysis of the tissue properties of the subject 14. As described in detail above, according to this invention, it is possible to detect an acoustic signal with high sensitivity, using a piezoelectric element comprising a solid solution system of a piezoelectric single crystal that contains at least lead titanate. Furthermore by using the piezoelectric single crystal as the piezoelectric material-polymer composite, it is possible to improve the sensitively of signal detection.

Moreover, since the piezoelectric single crystal has a high transparency in the visible light to infrared light wavelengths, and since the signal detecting unit can be constructed optically transparent by using a optically transparent epoxy resin for the acoustic matching layers and using a transparent conductive material for the electrodes, the light from the irradiation unit can pass through the signal detection unit, and be irradiated onto the subject. Furthermore, since the irradiation unit and the signal detection unit can be integrated into one unit, the size of the apparatus can be made compact. Moreover, since the detection efficiency of the acoustic signal is improved, higher accuracy monitoring is possible.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for non-invasive measurement of living body characteristics, comprising:
   a light source configured to generate light containing a specific wavelength component of 400 to 5000 nm;
   an irradiation unit configured to apply the light generated by the light source to a subject; and
   at least one acoustic signal detection unit including piezoelectric devices each formed of a piezoelectric single crystal containing lead titanate and configured to detect an acoustic signal resulting from energy of light applied to and absorbed by a specific substance present in or on the subject,
   wherein the piezoelectric single crystal has a transmittance of about 70% to the specific wavelength component of 400 to 6000 nm, and wherein the irradiation unit applies the light generated by the light source to the subject via the acoustic signal detection unit.

2. The apparatus according to claim 1, wherein the piezoelectric single crystal is represented by a general formula $$Pb[(B1, B2)_{1-x} Tl_x]O_3$$

wherein x =0.05 to 0.55, B1 represents an element selected from the group consisting of Zn, Mg, Ni, Sc, In, and Yb, and B2 represents an element selected from the group consisting of Nb and Ta.

3. The apparatus according to claim 1, wherein the piezoelectric devices of the acoustic signal detection unit are arranged two-dimensionally.

4. The apparatus according to claim 1, wherein the piezoelectric devices each have opposite major surfaces provided with respective transparent electrodes having transparency to the specific wavelength component.

5. The apparatus according to claim 1, wherein the acoustic signal detection unit is formed of a composite piezoelectric substance including the piezoelectric devices and a resin.

6. The apparatus according to claim 5, wherein the resin has transparency to the specific wavelength component.

7. The apparatus according to claim 6, wherein the piezoelectric devices have an optical refractive index and an optical transmittance substantially equivalent to an optical refractive index and an optical transmittance of the resin.

8. The apparatus according to claim 1, wherein the acoustic signal detection unit is formed by filling a resin in gaps between the piezoelectric devices.

9. The apparatus according to claim 1, further comprising a temperature control unit configured to control a temperature of a measurement site of the subject.

10. The apparatus according to claim 1, further comprising a sensor configured to detect contact of the acoustic signal detection unit with the subject.

11. The apparatus according to claim 10, further comprising a mechanism configured to move the acoustic signal detection unit in accordance with a degree of contact detected by the sensor.

12. The apparatus according to claim 1, wherein the at least one acoustic signal detection unit includes a plurality of acoustic signal detection units arranged two-dimensionally.

13. The apparatus according to claim 1, wherein the specific substance is glucose, and the applied light has at least one wavelength range selected from at least a range of 400 to 2500 nm.

14. The apparatus according to claim 1, wherein the specific substance is hemoglobin, and the applied light has at least one wavelength range selected from at least a range of 500 to 1600 nm.

* * * * *